(12) United States Patent  (10) Patent No.: US 7,896,817 B2
Garrison  (45) Date of Patent: Mar. 1, 2011

(54) BIOPSY DEVICE WITH MANUALLY ROTATED SAMPLE BARREL

(75) Inventor: William A. Garrison, Springdale, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 629 days.

(21) Appl. No.: 11/782,893

(22) Filed: Jul. 25, 2007

(65) Prior Publication Data

US 2008/0312554 A1 Dec. 18, 2008

Related U.S. Application Data

(63) Continuation-in-part of application No. 11/198,558, filed on Aug. 5, 2005, now Pat. No. 7,867,173.

(51) Int. Cl.
A61B 10/00 (2006.01)
(52) U.S. Cl. ............. 600/566; 600/562; 600/564; 600/565; 600/567
(58) Field of Classification Search ......... 600/562–572; 606/167–173, 180, 184–185; 604/326
See application file for complete search history.

(56) References Cited

U.S. PATENT DOCUMENTS

| | | | |
|---|---|---|---|
| 3,630,192 A | 12/1971 | Jamshidi |
| 4,051,852 A | 10/1977 | Villari |
| 4,600,014 A | 7/1986 | Beraha |
| 4,782,833 A | 11/1988 | Einhorn |
| 5,234,000 A | 8/1993 | Hakky et al. |
| 5,406,959 A | 4/1995 | Mann |
| 5,439,457 A | 8/1995 | Yoon |
| 5,526,822 A | 6/1996 | Burbank |
| 5,601,585 A | 2/1997 | Banik et al. |
| 5,645,209 A | 7/1997 | Green et al. |
| 5,649,547 A | 7/1997 | Ritchart |
| 5,769,086 A | 6/1998 | Ritchart |
| 5,775,333 A | 7/1998 | Burbank |
| 5,876,329 A | 3/1999 | Harhen |
| 5,928,164 A | 7/1999 | Burbank |

(Continued)

FOREIGN PATENT DOCUMENTS

EP 0 995 400 4/2000

(Continued)

OTHER PUBLICATIONS

Supplemental European Search Report dated Dec. 16, 2009 for Application No. EP06789155.

(Continued)

*Primary Examiner*—Jeffrey G Hoekstra
(74) *Attorney, Agent, or Firm*—Frost Brown Todd LLC

(57) ABSTRACT

A biopsy device and method may be used to obtain a tissue sample, such as a breast tissue biopsy sample. The biopsy device includes an outer cannula having a distal piercing tip, a cutter lumen, and a cutter tube that is rotated by an integral motor and manually translated past a side aperture in the outer cannula to sever a tissue sample. A sample capturing structure (e.g., sample barrel) has a plurality of sample cavities (e.g., radially symmetric, revolver handgun orientation) that are manually aligned one at a time to capture one or more samples.

18 Claims, 4 Drawing Sheets

U.S. PATENT DOCUMENTS

| | | |
|---|---|---|
| 5,964,716 A | 10/1999 | Gregoire |
| 5,980,469 A | 11/1999 | Burbank |
| 6,007,497 A | 12/1999 | Huitema |
| 6,017,316 A | 1/2000 | Ritchart |
| 6,077,230 A | 6/2000 | Gregoire |
| 6,083,177 A | 7/2000 | Kobren et al. |
| 6,086,544 A | 7/2000 | Hibner |
| 6,120,462 A | 9/2000 | Hibner |
| 6,142,946 A | 11/2000 | Hwang et al. |
| 6,213,957 B1 | 4/2001 | Milliman et al. |
| 6,228,055 B1 | 5/2001 | Foerster |
| 6,231,522 B1 | 5/2001 | Voegele |
| 6,273,862 B1 | 8/2001 | Privitera |
| 6,402,701 B1 | 6/2002 | Kaplan et al. |
| 6,428,486 B2 | 8/2002 | Ritchart et al. |
| 6,485,436 B1 | 11/2002 | Truckai et al. |
| 6,544,194 B1 | 4/2003 | Kortenbach et al. |
| 6,620,111 B2 | 9/2003 | Stephens et al. |
| 6,638,235 B2 | 10/2003 | Miller et al. |
| 6,659,338 B1 | 12/2003 | Dittmann et al. |
| 6,758,824 B1 | 7/2004 | Miller |
| 6,849,080 B2 | 2/2005 | Lee et al. |
| 7,025,098 B2 | 4/2006 | Osborne |
| 7,226,424 B2 | 6/2007 | Ritchart |
| 7,445,739 B2 | 11/2008 | Tsonton et al. |
| 7,575,556 B2 * | 8/2009 | Speeg et al. ................. 600/566 |
| 2002/0082518 A1 | 6/2002 | Weiss et al. |
| 2002/0120212 A1 | 8/2002 | Ritchart et al. |
| 2003/0199753 A1 | 10/2003 | Hibner et al. |
| 2004/0153003 A1 | 8/2004 | Cicenas et al. |
| 2005/0049521 A1 | 3/2005 | Miller et al. |
| 2005/0165328 A1 | 7/2005 | Heske et al. |
| 2005/0215921 A1 | 9/2005 | Hibner |
| 2005/0215922 A1 | 9/2005 | Tsonton et al. |
| 2006/0041230 A1 | 2/2006 | Davis |
| 2006/0074344 A1 | 4/2006 | Hibner |
| 2006/0074345 A1 | 4/2006 | Hibner et al. |
| 2006/0258955 A1 | 11/2006 | Hoffman et al. |
| 2007/0032741 A1 | 2/2007 | Hibner et al. |
| 2007/0032742 A1 | 2/2007 | Monson |
| 2007/0032743 A1 | 2/2007 | Hibner |
| 2007/0213630 A1 | 9/2007 | Beckman et al. |
| 2007/0239067 A1 | 10/2007 | Hibner |
| 2008/0004545 A1 | 1/2008 | Garrison |
| 2008/0195066 A1 * | 8/2008 | Speeg et al. ................. 604/326 |

FOREIGN PATENT DOCUMENTS

| | | |
|---|---|---|
| EP | 1 520 518 | 4/2005 |
| EP | 1 832 234 | 12/2007 |
| EP | 1932482 | 6/2008 |
| WO | WO 03/077768 | 9/2003 |
| WO | WO 2004/052212 | 6/2004 |
| WO | WO 2006/124489 | 11/2006 |
| WO | WO 2007/019152 | 2/2007 |
| WO | WO 2007/021904 | 2/2007 |
| WO | WO 2007/112751 | 10/2007 |

OTHER PUBLICATIONS

EnCor MRI Specifications and Breast Biopsy System, SenoRx, 2005, pp. 102.
ISR dated Jul. 18, 2007 for PCT Application No. PCT/US 06/30022.
ESR dated Dec. 20, 2007 for EPO Application No. 07253220.
International Search Report dated Dec. 18, 2008 for Application No. PCT/US2008/058627.
European Search Report dated Nov. 14, 2007 for Application No. 07250926.
European Search Report dated Apr. 3, 2009 for Application No. 08252518.
European Search Report dated Apr. 3, 2009 for Application No. 08252524.
European Examination Report dated Mar. 19, 2009 for Application No. 07250926.
Patentability Report and Written Opinion dated Feb. 5, 2008 for Application No. PCT/US2006/030022.
U.S. Appl. No. 11/198,558, filed Aug. 5, 2005, Hibner, John A.
U.S. Appl. No. 60/869,736, filed Dec. 13, 2006, Hibner, John A.
U.S. Appl. No. 60/874,792, filed Dec. 13, 2006, Hibner, John A.
Non-final Rejection dated Mar. 20, 2008 for U.S. Appl. No. 11/782,963.
Non-final Rejection dated Apr. 4, 2008 for U.S. Appl. No. 11/736,117.
Final Rejection dated Sep. 26, 2008 for U.S. Appl. No. 11/782,963.
Non-Final Rejection dated Oct. 6, 2008 for U.S. Appl. No. 11/736,117.
International Search Report dated Sep. 27, 2007 for Application No. PCT/US06/30022.
European Communication dated Apr. 26, 2010 for Application No. 08252524.

* cited by examiner

BIOPSY DEVICE WITH MANUALLY ROTATED SAMPLE BARREL

CROSS REFERENCE TO RELATED APPLICATIONS

The present application is a continuation-in-part of the co-pending and commonly-owned U.S. patent application Ser. No. 11/198,558, "BIOPSY DEVICE WITH REPLACEABLE PROBE AND INCORPORATING VIBRATION INSERTION ASSIST AND STATIC VACUUM SOURCE SAMPLE STACKING RETRIEVAL" to Hibner et al., filed Aug. 5, 2005, the disclosure of which is hereby incorporated by reference in its entirety.

BACKGROUND

Embodiments of the present invention relate in general to biopsy devices, and more particularly to biopsy devices having a cutter for severing tissue, and even more particularly to biopsy devices for multiple sampling with a probe remaining inserted.

During a core needle biopsy, a small tissue sample may be removed, allowing for a pathological assessment of the tissue, including an assessment of the progression of any cancerous cells that are found. The following patent documents disclose various core biopsy devices and are each incorporated herein by reference in their entirety: U.S. Pat. No. 6,273,862, issued Aug. 14, 2001; U.S. Pat. No. 6,231,522, issued May 15, 2001; U.S. Pat. No. 6,228,055, issued May 8, 2001; U.S. Pat. No. 6,120,462, issued Sep. 19, 2000; U.S. Pat. No. 6,086,544, issued Jul. 11, 2000; U.S. Pat. No. 6,077,230, issued Jun. 20, 2000; U.S. Pat. No. 6,017,316, issued Jan. 25, 2000; U.S. Pat. No. 6,007,497, issued Dec. 28, 1999; U.S. Pat. No. 5,980,469, issued Nov. 9, 1999; U.S. Pat. No. 5,964,716, issued Oct. 12, 1999; U.S. Pat. No. 5,928,164, issued Jul. 27, 1999; U.S. Pat. No. 5,775,333, issued Jul. 7, 1998; U.S. Pat. No. 5,769,086, issued Jun. 23, 1998; U.S. Pat. No. 5,649,547, issued Jul. 22, 1997; U.S. Pat. No. 5,526,822, issued Jun. 18, 1996; and U.S. Pub. No. 2003/0199753, published Oct. 23, 2003 to Hibner et al.

Some biopsy devices may be regarded as "long stroke" or "short stroke." For instance, several "short stroke" biopsy devices are described in the following published patent applications: U.S. patent application Ser. No. 10/676,944 (U.S. Pub. No. 2005/0215921), entitled "Biopsy Instrument with Internal Specimen Collection Mechanism," filed Sep. 30, 2003 in the name of Hibner et al.; and U.S. patent application Ser. No. 10/732,843, (U.S. Pub. No. 2004/0153003), entitled "Biopsy Device with Sample Tube," filed Dec. 10, 2003 in the name of Cicenas et al. The disclosure of each of those published patent applications is incorporated by reference herein. In some embodiments, the cutter is cycled across the side aperture, reducing the sample time. Several alternative specimen collection mechanisms are described that draw samples through the cutter tube, which may allow for taking multiple samples without removing the probe from the breast.

In U.S. patent application Ser. No. 10/953,834, entitled "Biopsy Apparatus and Method" to Hibner et al., filed Sep. 29, 2004 (U.S. Pub. No. 2006/0074345), the disclosure of which is hereby incorporated by reference in its entirety, tissue samples are drawn by vacuum proximally through the cutter tube into a serial tissue stacking assembly that preserves the order of sample taking, that can be visually observed through a transparent lumen, and that serves as a transport container to take for a pathology examination. Yet another biopsy device is disclosed in co-pending U.S. Patent Application Ser. No. 60/869,736, entitled "Biopsy System" to Hibner et al., filed Dec. 13, 2006, the disclosure of which is hereby incorporated by reference in its entirety.

Additional sample storage devices are disclosed in co-pending U.S. Patent Appln. Ser. No. 60/874,792, entitled "Biopsy Sample Storage" to Hibner et al., filed Dec. 13, 2006, the disclosure of which is hereby incorporated by reference in its entirety. Still more sample storage devices are disclosed in U.S. patent application Ser. No. 11/782,963, entitled "Trigger Fired Radial Plate Specimen Retrieval Biopsy Instrument" to Garrison, filed on even date herewith, the disclosure of which is hereby incorporated by reference in its entirety.

While a variety of tissue storage devices has been made and used, it is believed that no one prior to the inventor has made or used a device as recited in the present claims.

BRIEF DESCRIPTION OF THE DRAWINGS

While the specification concludes with claims particularly pointing out and distinctly claiming the present invention, it is believed the same will be better understood by reference to the following description, taken in conjunction with the accompanying drawings in which:

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 1:
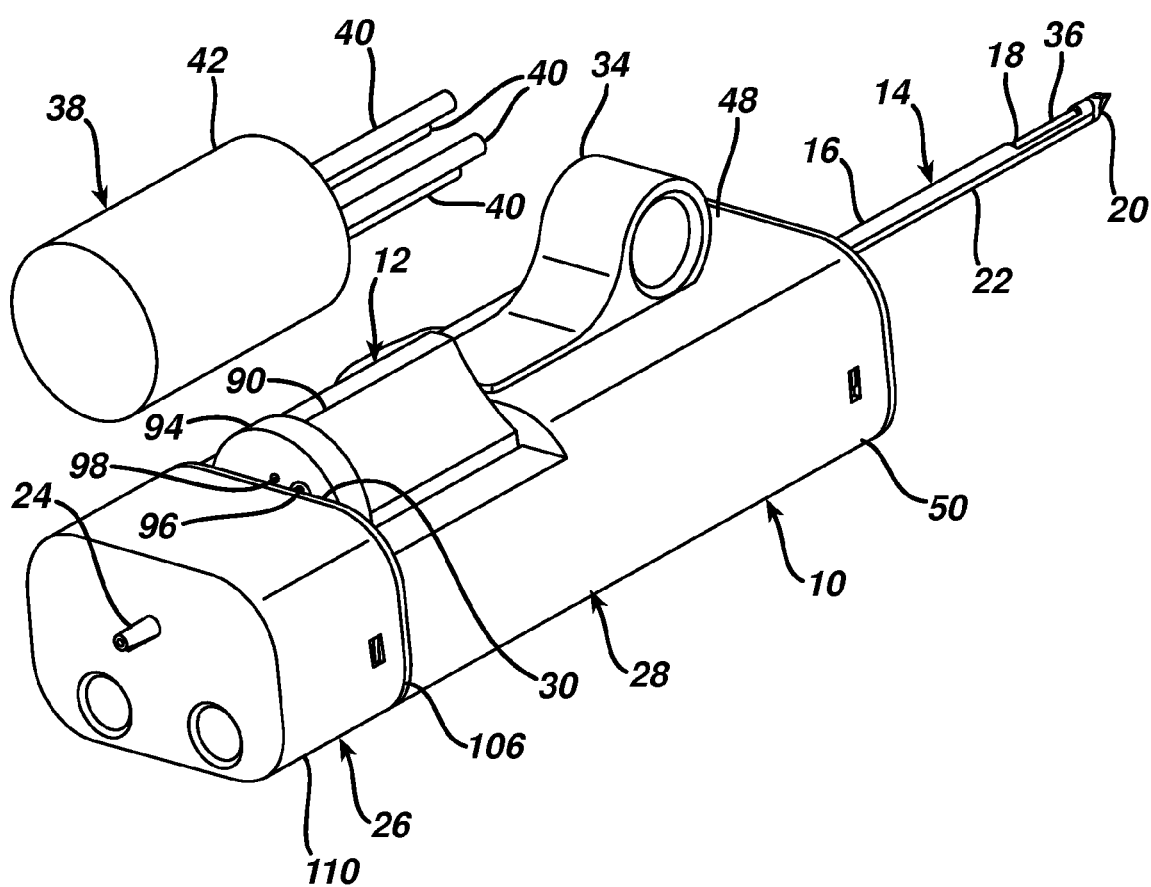
FIG. 1 is a perspective view from a right side of a biopsy device with sample extraction tool.

Turning to the drawings, wherein like numerals denote like components throughout the several views, in FIGS. 1-4, with particular reference to FIG. 1, a biopsy device 10 includes a sample storage barrel 12 rotated about a central axis, which in the illustrative version is longitudinal, parallel to and slightly offset from a longitudinal axis of a core biopsy probe 14. The probe 14 includes a cutter lumen 16 having a side aperture 18 just proximal to a distal piercing tip 20. In other embodiments, tip 20 is blunt, and in additional non-exhaustive embodiments, tip 20 is open. A lateral lumen 22 attached alongside the cutter lumen 16 communicates distally to an area within the cutter lumen 16 proximate to the side aperture 18 for providing vacuum assistance for prolapsing tissue into the side aperture 18, and proximally communicates to a vacuum hose nib 24 on a proximal portion 26 of a handle 28. An upper portion of the sample storage barrel 12 is exposed out of a barrel cavity 30 of a distal portion 32 of the handle 28. The proximal portion 26 of the handle abuts a proximal surface of the sample storage barrel 12. A slide trigger 34 is depicted as at a distal position upon an upper surface of the distal portion 32 of the handle 28, positioning a cutter tube 36 distally within the cutter lumen 16, depicted closing the side aperture 18. Of course, any other suitable configurations, components, and relationships between such components, may be used in addition to or as an alternative to the above-described components. It will also be appreciated that certain embodiments of the biopsy device 10 may be configured such that the biopsy device may be manipulated by a single hand of a user during use of the biopsy device 10 (e.g., while using the biopsy device 10 to obtain tissue samples).

The sample storage barrel 12 of the present example may be disengaged from the barrel cavity 30 and perhaps replaced with an empty barrel 12 for capturing additional tissue samples. A sample extraction tool 38 may be employed to simultaneously push the tissue samples out of the disengaged sample storage barrel 12. It should be appreciated that four pusher rods 40 extending in parallel and radially spaced fashion from a tool handle 42 are depicted in the illustrative version; however, various numbers may be configured as desired. In other words, a sample storage barrel 12 may be configured to hold any suitable number of tissue samples, and an extraction tool 38 may have any suitable number of pusher rods (which need not necessarily correspond with the number of tissue samples a storage barrel is capable of holding). Other suitable configurations for a sample extraction tool 38 will be apparent to those of ordinary skill in the art.

Figure 2:
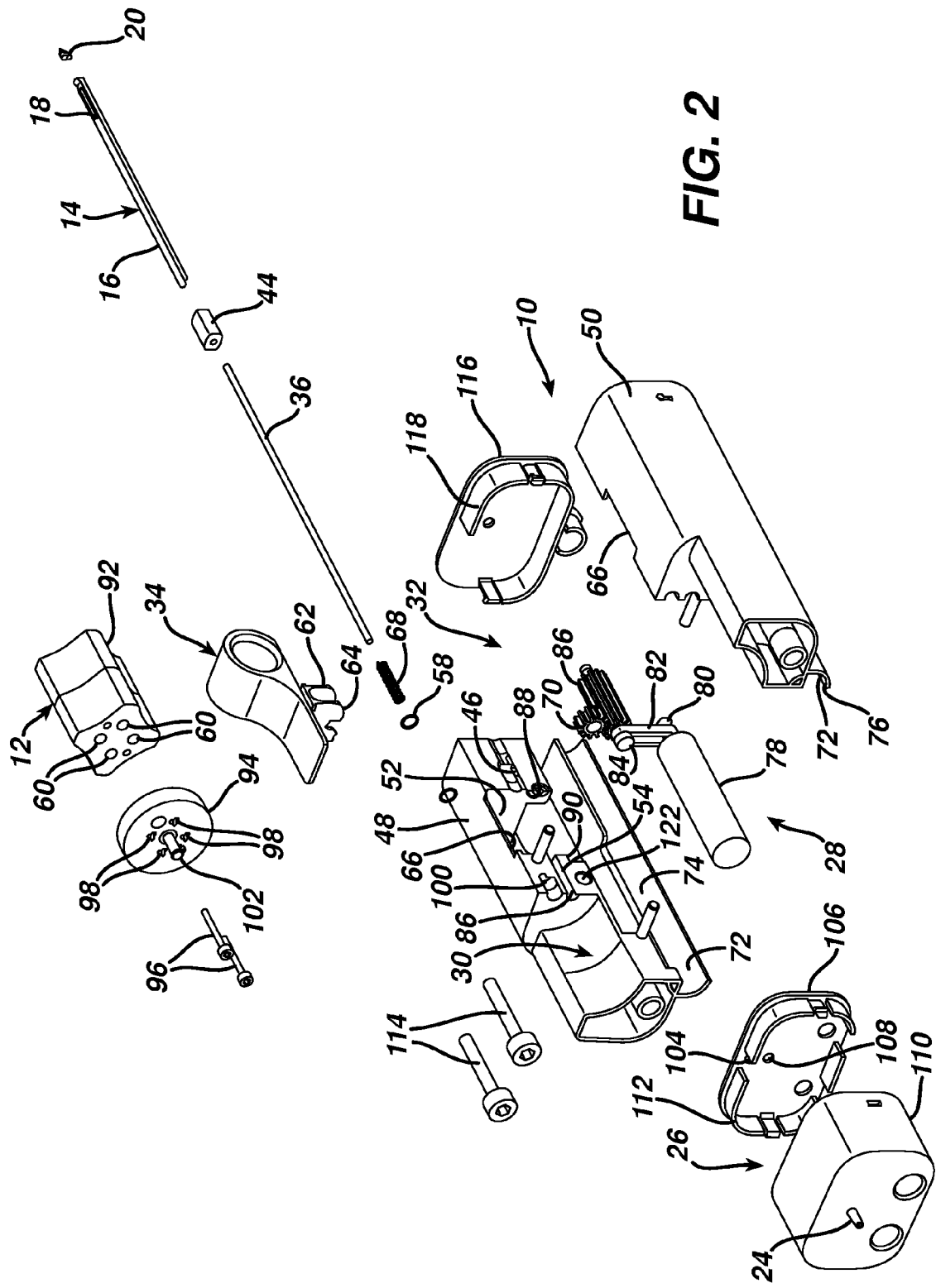
FIG. 2 is an exploded view of the biopsy device of FIG. 1.

With particular reference to FIG. 2, a proximal end of the core biopsy probe 14 is received with a union sleeve 44 that is engaged with a sleeve recess 46 defined in both a left and right handle body 48, 50 that communicates proximally to a translation yoke cavity 52, which in turn communicates with a longitudinally aligned sample passage 54 to proximally terminate in an O-ring groove 56.

Figure 3:
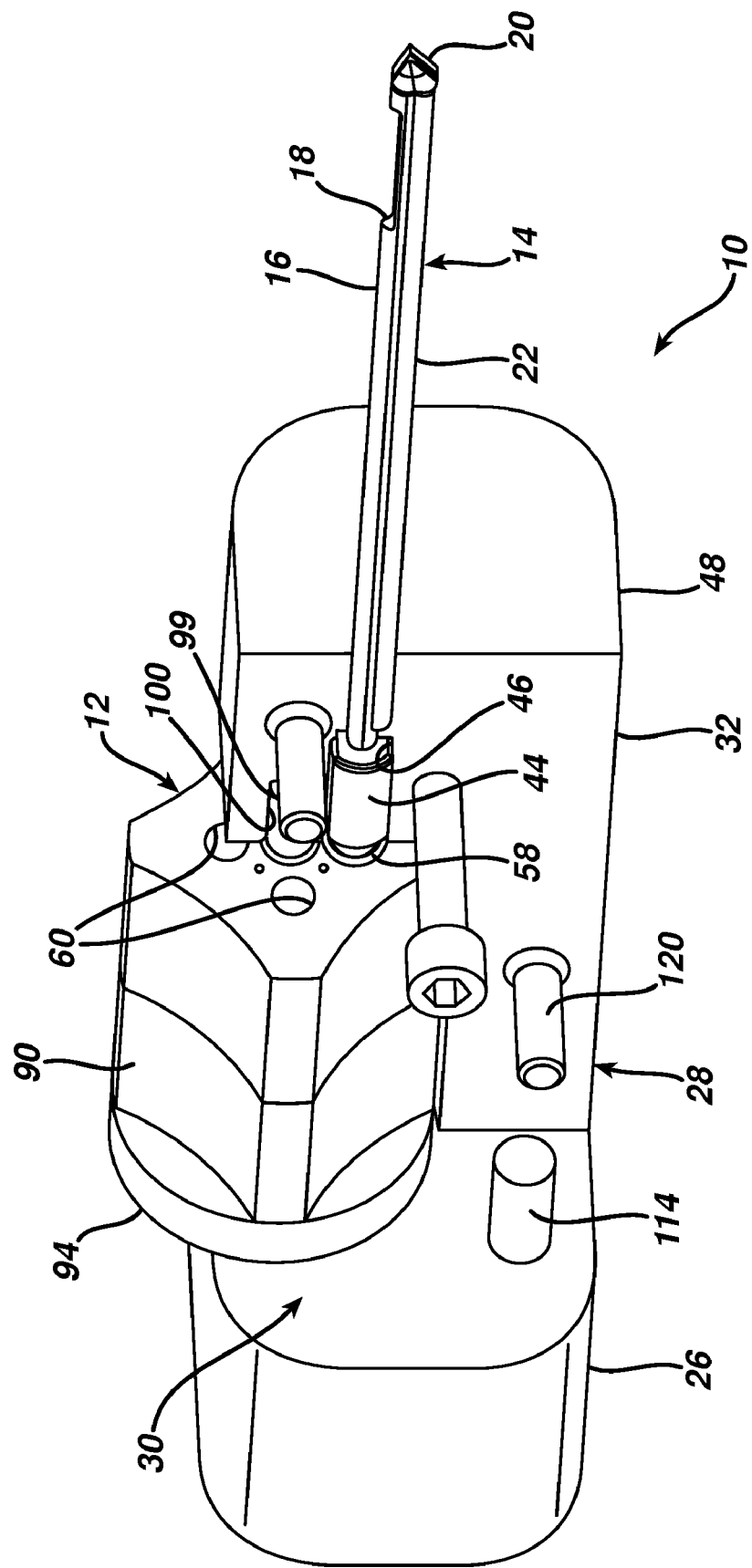
FIG. 3 is an isomeric view of a left handle body, proximal portion of a handle, and probe of the biopsy device of FIG. 1.

In FIG. 3, a proximal O-ring 58 received in the O-ring groove 56 dynamically seals to a distal face of the sample storage barrel 12, and more particularly to a selected one of four sample holding chambers 60 that are longitudinally parallel and radially spaced through the sample storage barrel 12. The proximal end of the cutter tube 36 remains within the sample passage 54 while being translated to distal and proximal positions by fore and aft downward projecting transverse gripping flanges 62, 64 attached by a longitudinal rib (not shown) that extends through a top longitudinal slot 66 formed between the left and right handle bodies 48, 50 extending from the slide trigger 34. Other suitable configurations, components, and relationships between such components, will be apparent to those of ordinary skill in the art.

Figure 4:
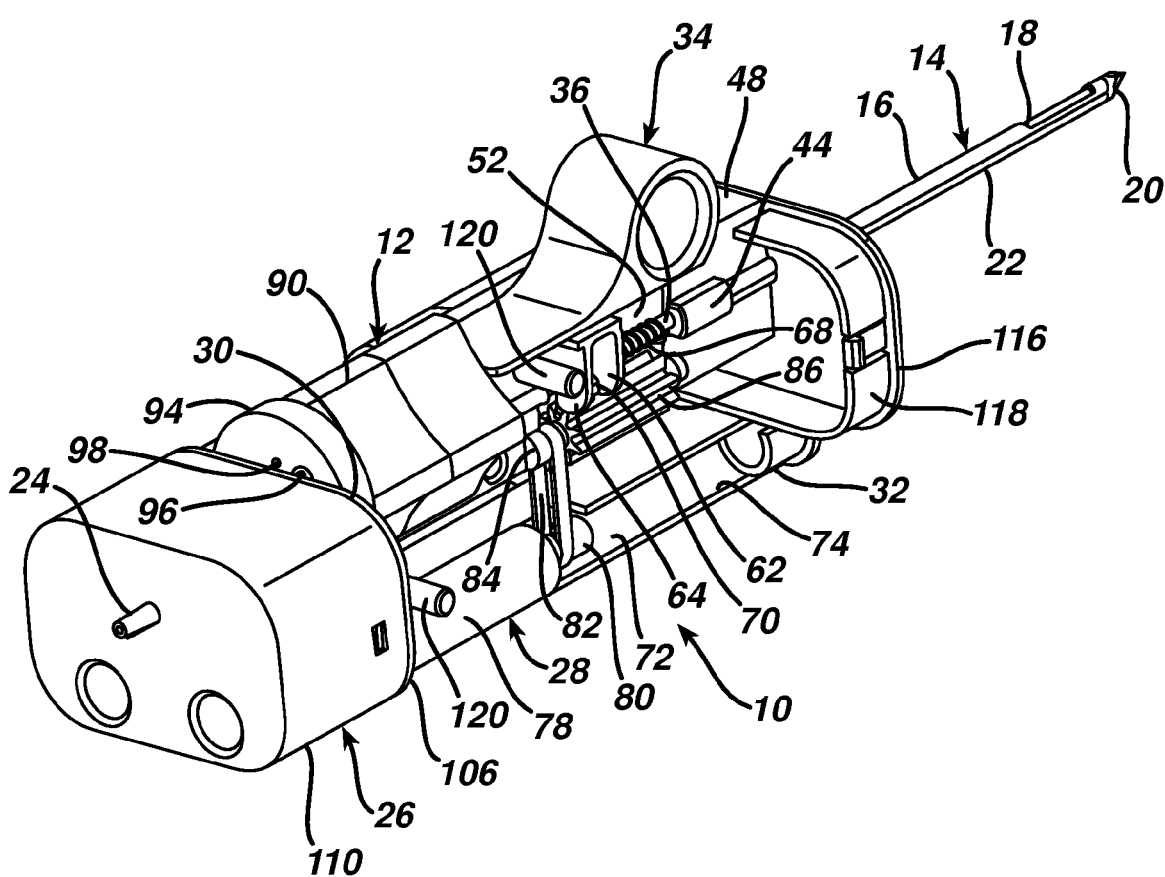
FIG. 4 is right, aft isometric view of the biopsy device of FIG. 1 with a right handle body omitted.

In the present example, cutter tube 36 is translated by manual actuation of slide trigger 34 (e.g., by manually translating slide trigger 34 distally or proximally) to sever tissue prolapsed into side aperture 18. However, it will be appreciated that a motor (not shown) or other device may be used to translate cutter tube 36. As shown in FIG. 4, a compression spring 68 is received over a portion of the cutter tube 36 between the fore transverse gripping flange 62 and a distal face of the translation yoke cavity 52, providing a proximal restoring force when the slide trigger 34 is distally actuated. Of course, as with any other component described herein, any suitable alternative or supplement to compression spring 68 may be used, or it may be omitted altogether.

With further reference to FIG. 2, a cutter spur gear 70 is attached to a portion of the cutter tube 36 that resides between the fore and aft transverse gripping flanges 62, 64. A longitudinally elongate rotation drive motor cavity 72 is defined by left and right channels 74, 76 along a bottom of the left and right handle bodies 48, 50 and encompasses a rotation drive motor 78. Drive motor 78 may receive power from any suitable source. A drive pulley 80 extending distally from the rotation drive motor 78 receives a lower loop of a rotation drive belt 82. An upper loop of the rotation drive belt 82 passes over a proximal extending pulley 84 of an elongate rotation spur gear 86 whose distal and proximal shaft ends are received respectively in distal and proximal hub recesses 88, 90 formed between the left and right handle bodies 48, 50 and communicating inwardly to the translation yoke cavity 52. The elongate rotation spur gear 86 is in gear engagement with the cutter spur gear 70 along the length of its translation to impart a rotation to the cutter tube 36. It will be appreciated, however, that any suitable alternative mechanism may be used to rotate cutter tube 36, to the extent that cutter tube 36 is configured to rotate at all.

In some embodiments, cutter tube 36 remains in constant rotation, independent of any actuation of slide trigger 34. For instance, a user actuated switch (not shown) may be provided on/in biopsy device 10, as a foot switch, or otherwise, for a user to activate drive motor 78 to cause rotation of cutter tube 36. In other embodiments, a switch (not shown) may be operably coupled with slide trigger 34, such that drive motor 78 begins rotating cutter tube 36 as soon as slide trigger 34 is moved distally from a default position or is otherwise engaged or actuated. Alternatively, any other suitable structures, devices, or methods of activating a drive motor 78 may be used. In other embodiments, drive motor 78 is omitted altogether, and cutter tube 36 rotates using some other device or technique, or simply does not rotate at all.

The sample storage barrel 12 of the present example is assembled from a barrel body 92 having four sample holding chambers 60 and having radially spaced longitudinal ridges to serve as surfaces for manually rotating the barrel 12. A blocking disk 94 is fastened to a proximal face of the barrel body 92 by two small bolts 96. A tight pattern of small through holes 98 registered to each sample holding chamber 60 forming a fluid filter. With a vacuum applied to a sample holding chamber 60 that is aligned with the vacuum hose nib 24 and the cutter tube 36, a tissue sample that has been severed by the cutter tube 36 will be drawn into the sample holding chamber 60. To the extent that fluid is also drawn into the sample holding chamber 60, the fluid may pass proximally through holes 98; yet holes 98 may be sized to prevent proximal passage of the tissue sample. It will therefore be appreciated that blocking disk 94 of the present example retains a biopsy tissue sample in each sample holding chamber 60 that is rotated into alignment with the sample passage 54. The barrel body 92 includes a distally directed axle end 99 (FIG. 3) that is received within a barrel hub recess 100 formed in the left and right handle bodies 48, 50 above the sample passage 54. The blocking disk 94 includes a proximally directed axle end 102 that is received for rotation in an upper central hole 104 in a transverse oval cap 106. Still other suitable variations, substitutes, and supplements for sample storage barrel 12 will be apparent to those of ordinary skill in the art.

A vacuum orifice 108 positioned just below the upper central hole 104 aligns with the fluid filter 98 in the blocking disk 94 registered to the selected sample holding chamber 60, the orifice 108 communicating with the vacuum hose nib 24 supported by a distally open oval cup 110. The proximal portion 26 of the handle 28 is assembled by a snap fit ridges 112 extending proximally from the transverse oval cap 106 into the distally open oval cup 110 and then attached to the left and right handle bodies 48, 50 by two large fasteners 114. A distal transverse cap 116 having proximally extending snap fit ridges 118 engages the distal openings in the left and right handle bodies 48, 50, which are laterally attached to one another by inwardly expending pins 120 from one received in locking holes 122 in the other. It will be appreciated, however, that these components may be configured in any other suitable way and may have any other suitable relationships.

While the barrel 12 of the present example is rotated manually (e.g., such as by a user rotating the barrel 12 by directly pushing it to rotate it in a desired direction, etc.), barrel 12 may be rotated in a variety of ways in other embodiments. For instance, a mechanism (not shown) may be provided in communication with slide trigger 34, whereby each distal actuation of slide trigger 34 combined with a subsequent proximal retraction of slide trigger 34 causes barrel 12 to rotate in a manner sufficient to align the next empty holding chamber 60 with cutter tube 36. As another merely illustrative example, a transmission and clutch (neither shown) may be provided in communication with drive motor 78, whereby each distal actuation of slide trigger 34 combined with a subsequent proximal retraction of slide trigger 34 causes the clutch to couple the drive motor 78 with the barrel 12 via the transmission in a manner sufficient to transfer rotation from the drive motor 78 to the barrel 12 in a manner sufficient to align the next empty holding chamber 60 with cutter tube 36. Suitable gearing ratios and other methods for accomplishing such rotation of barrel 12 by drive motor 78 will be apparent to those of ordinary skill in the art. Furthermore, one or more locking mechanisms (not shown) may be provided on or within biopsy device 10 to prevent inadvertent rotation of barrel 12 during biopsy procedures.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein, will only be incorporated to the extent that no conflict arises between that incorporated material and the existing disclosure material.

While preferred embodiments of the present invention have been shown and described herein, it will be obvious to those skilled in the art, given the benefit of the present disclosure, that such embodiments are provided by way of example only. Numerous variations, changes, and substitutions will now occur to those skilled in the art without departing from the spirit and scope of the appended claims.

For example, a thumbwheel may be included that allows rotation of the probe 14 cannula to orient the side aperture 18.

For another example, while a motorized rotation mechanism is depicted, applications consistent with the present invention may include a transmission that converts the translation motion further into a rotation motion imparted to the cutter tube. For another example, while manual translation of a cutter tube 36 may provide certain advantages such as tactile feedback to the clinician, applications consistent with the present invention may include motorized translation or rotation that is converted from the translation motion of the cutter. Furthermore, hydraulic, pneumatic, or any other type of rotation and/or translation devices may be used.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed an sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. the sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A method of obtaining a plurality of biopsy tissue samples, the method comprising:
   (a) providing a biopsy device, the biopsy device comprising:
      (i) a biopsy probe cannula having a distal end and a distal opening, wherein the biopsy probe cannula defines a probe axis,
      (ii) a cutter tube translatable within the probe cannula,
      (iii) a handle coupled with the probe cannula, wherein the handle has a feature configured to be coupled with a vacuum source, and
      (iv) a storage unit engaged with the handle, wherein the storage unit has a plurality of tissue storage compartments, wherein the storage unit is configured to receive at least one tissue sample within each of the tissue storage compartments, wherein the storage unit is configured to rotate relative to the handle, about a rotation axis, in order to receive tissue samples communicated proximally through the cutter tube, wherein the rotation axis is positioned lateral to the probe axis;
   (b) obtaining a first biopsy tissue sample from a patient, wherein the first biopsy tissue sample is communicated to a first tissue storage compartment of the plurality of tissue storage compartments via the cutter tube by a vacuum urging the first tissue sample proximally through the cutter tube;

(c) manually rotating the storage unit about the rotation axis to substantially align a second tissue storage compartment of the plurality of tissue storage compartments with the cutter tube, wherein the act of manually rotating the storage unit is carried out without using a motor to rotate the storage unit; and (d) obtaining a second biopsy tissue sample from a patient, wherein the second biopsy tissue sample is communicated to the second tissue storage compartment via the cutter tube by a vacuum urging the second tissue sample proximally through the cutter tube.

2. The method of claim 1, wherein the storage unit has a plurality of longitudinal ridges, wherein the act of manually rotating the storage unit about the rotation axis comprises engaging at least one of the longitudinal ridges and manually pushing the storage unit to rotate the storage unit.

3. The method of claim 2, wherein the storage unit comprises a barrel defining the rotation axis.

4. The method of claim 3, wherein the longitudinal ridges are angularly spaced about the rotation axis and along an outer perimeter of the barrel.

5. The method of claim 1, wherein the cutter tube defines a longitudinal axis, wherein the rotation axis is substantially parallel with the longitudinal axis defined by the cutter tube.

6. The method of claim 1, wherein each tissue storage compartment comprises a discrete lumen defined by the storage device.

7. The method of claim 1, wherein the storage unit has a proximal blocking component configured to restrict proximal communication of tissue samples relative to the storage unit.

8. The method of claim 7, wherein the blocking component has a plurality of apertures configured to permit communication of fluid through the apertures while preventing communication of tissue samples through the apertures.

9. The method of claim 1, wherein the distal opening of the probe cannula comprises a transverse tissue receiving window located proximal from but near the distal end of the probe cannula.

10. The method of claim 1, wherein the probe cannula comprises a cutter lumen and a vacuum lumen, wherein the cutter lumen is configured to receive the cutter tube, wherein the vacuum lumen is separate from but in fluid communication with the cutter lumen.

11. The method of claim 1, wherein the act of obtaining the first biopsy tissue sample comprises translating the cutter tube relative to the probe cannula.

12. The method of claim 11, wherein the act of obtaining obtaining the first biopsy tissue sample further comprises rotating the cutter tube relative to the probe cannula.

13. The method of claim 12, wherein the act of rotating the cutter tube comprises activating a drive motor to rotate the cutter tube.

14. The method of claim 1, further comprising:
(a) providing a sample extraction tool comprising a plurality of radially spaced and longitudinally parallel pushers registered for insertion simultaneously through the tissue storage compartments;
(b) removing the storage unit from the handle; and
(c) inserting the pushers through the tissue storage compartments to remove the first and second biopsy tissue samples from the storage unit.

15. The method of claim 1, wherein the biopsy device further comprises a port configured to couple with an external vacuum source, wherein the port is further configured to communicate a vacuum from the external vacuum source to the proximal end of the cutter tube.

16. The method of claim 15, wherein the port configured to couple with an external vacuum source is proximal to the storage unit.

17. The method of claim 16, wherein the port configured to couple with an external vacuum source is oriented along a port axis that is substantially parallel to the probe axis.

18. A method of obtaining a plurality of biopsy tissue samples using a biopsy device, wherein the biopsy device comprises a biopsy probe cannula, a cutter tube, a handle, and a storage unit, wherein the biopsy probe cannula has a distal end and a distal opening, wherein the biopsy probe cannula defines a probe axis, wherein the cutter tube is translatable within the probe cannula, wherein the handle is coupled with the probe cannula, wherein the storage unit is engaged with the handle, wherein the storage unit has a plurality of tissue storage compartments, wherein the storage unit is configured to receive at least one tissue sample within each of the tissue storage compartments, wherein the storage unit is configured to rotate relative to the handle, about a rotation axis, in order to receive tissue samples communicated proximally through the cutter tube, wherein the rotation axis is positioned lateral to the probe axis, the method comprising:
(a) obtaining a first biopsy tissue sample from a patient, wherein the first biopsy tissue sample is communicated to a first tissue storage compartment of the plurality of tissue storage compartments via the cutter tube by a vacuum urging the first tissue sample proximally through the cutter tube;
(b) manually rotating the storage unit about the rotation axis to substantially align a second tissue storage compartment of the plurality of tissue storage compartments with the cutter tube, wherein the act of manually rotating the storage unit is carried out without using a motor to rotate the storage unit; and
(c) obtaining a second biopsy tissue sample from a patient, wherein the second biopsy tissue sample is communicated to the second tissue storage compartment via the cutter tube by a vacuum urging the second tissue sample proximally through the cutter tube.

* * * * *